(12) United States Patent
Tobin

(10) Patent No.: US 6,350,855 B1
(45) Date of Patent: Feb. 26, 2002

(54) HUMAN INTERLEUKIN-11 RECEPTOR

(75) Inventor: James Tobin, Newton, MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 08/929,846

(22) Filed: Sep. 15, 1997

Related U.S. Application Data

(60) Division of application No. 08/663,584, filed on Jun. 14, 1996, which is a continuation-in-part of application No. 08/362,304, filed on Dec. 22, 1994, now abandoned.

(51) Int. Cl.$^7$ ............... C07K 14/715; C12N 15/12
(52) U.S. Cl. .......... 530/350; 435/69.1; 435/71.1; 435/71.2; 435/172.3; 435/320.1; 435/252.3; 435/325
(58) Field of Search ............... 530/350; 435/69.1, 435/71.1, 71.2, 172.3, 325, 252.3, 320.1

(56) References Cited

PUBLICATIONS

Takeshita et al. (1992) Science vol. 257, pp. 379–382, 1992.*
Murata et al (1992) J. Exptal. Medicine vol. 175, pp.341–351, 1992.*
Yin et al. (1992) J. of Biol. Chem. vol. 267, No. 12, pp. 8347–8351, 1992.*

* cited by examiner

*Primary Examiner*—John Ulm
*Assistant Examiner*—Prema Mertz
(74) *Attorney, Agent, or Firm*—Mintz Levin; Ivor R. Elrifi; David E. Johnson

(57) ABSTRACT

Polynucleotides encoding the human IL-11 receptor and fragments thereof are disclosed. IL-11 receptor proteins, methods for their production, inhibitors of binding of human IL-11 and its receptor and methods for their identification are also disclosed.

13 Claims, 4 Drawing Sheets

```
                           SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
           (A) LENGTH: 2456 base pairs
           (B) TYPE: nucleic acid
           (C) STRANDEDNESS: double
           (D) TOPOLOGY: linear (ii) MOLECULE TYPE: cDNA (iii) HYPOTHETICAL: NO (ix) FEATURE:
           (A) NAME/KEY: CDS
           (B) LOCATION: 734..1999

(xi) SEQUENCE DESCRIPTION: SEQ ID NO:1:

TCGCCCACCC CCAGCCTCTG GCAGCAGCCA GGGCATCTGG ATCTGCTTAA CTACACAGCC         60

CCAGCCTGCA CCCTAGCCCC ATCCAGCTTC ACAAACTGGA GACCAACGAA GTGTCAAGAG        120

CCAGGCCCAG CTGAGTGGCC CAAGTAGCCA GACCAAGGAG CCAGGTTCAG GCGAGAAGCC        180

TGGCAGCCAG GGCAGGGGTG GGCCTCAGGG TGGGAGTGCA GGATGGGCTC AGATCCATGA        240

TGACACCCTT CCCCCAGGGT GATAAGGTCT GCCTAGGTTA ATCAGAGGCA GTGATAAGCC        300

CTGGACCAGG TGGGGGTAAA TACCAGAATT CCCAACAGCT GGACTGGAGG GGTTAATGGG        360

AGTGGCTGAG CTGGTGCCAG TGCTTGGTGC CAGGGGTGGG CGCCAAGGGC AGTGGAGGGG        420

GAGTTGCTGG CACAGTCTGT TGCCTCCGGC TTTTGTTCTG GGCCCTAAGC CCAGGACTGA        480

GATGGAGGGT GTGAGGGGGT GTGTGTGTCC GTGTGTGTGT GTGTGTGTGT GTGCGCGCGC        540

ACGCACATGC AAAGCACTGG GTATACAGTG GGAAAGGGGA CCTCAGGTCA GTTCCCGCAG        600

TGATTTCTAA CAGCCTTACC CCACTTGGTG CATCAATTTT TCTCCTAGGA AGCCTCAGTT        660

TTGGAGAGGA AGAGCCAGGC TTTAGCCTCC CATCTCAGGG GTCGGGGATT TTTGACTCTA        720

CCTCTCCCCA CAG ATG AGC AGC AGC TGC TCA GGG CTG AGC AGG GTC CTG          769
                  Met Ser Ser Ser Cys Ser Gly Leu Ser Arg Val Leu
                   1               5                  10

GTG GCC GTG GCT ACA GCC CTG GTG TCT GCC TCC TCC CCC TGC CCC CAG          817
   Val Ala Val Ala Thr Ala Leu Val Ser Ala Ser Ser Pro Cys Pro Gln
            15                  20                  25
```

```
                                                                -continued

GCC TGG GGC CCC CCA GGG GTC CAG TAT GGG CAG CCA GGC AGG TCC GTG       865
Ala Trp Gly Pro Pro Gly Val Gln Tyr Gly Gln Pro Gly Arg Ser Val
         30                  35                  40

AAG CTG TGT TGT CCT GGA GTG ACT GCC GGG GAC CCA GTG TCC TGG TTT       913
Lys Leu Cys Cys Pro Gly Val Thr Ala Gly Asp Pro Val Ser Trp Phe
 45                  50                  55                  60

CGG GAT GGG GAG CCA AAG CTG CTC CAG GGA CCT GAC TCT GGG CTA GGG       961
Arg Asp Gly Glu Pro Lys Leu Leu Gln Gly Pro Asp Ser Gly Leu Gly
                 65                  70                  75

CAT GAA CTG GTC CTG GCC CAG GCA GAC AGC ACT GAT GAG GGC ACC TAC      1009
His Glu Leu Val Leu Ala Gln Ala Asp Ser Thr Asp Glu Gly Thr Tyr
             80                  85                  90

ATC TGC CAG ACC CTG GAT GGT GCA CTT GGG GGC ACA GTG ACC CTG CAG      1057
Ile Cys Gln Thr Leu Asp Gly Ala Leu Gly Gly Thr Val Thr Leu Gln
         95                 100                 105

CTG GGC TAC CCT CCA GCC CGC CCT GTT GTC TCC TGC CAA GCA GCC GAC      1105
Leu Gly Tyr Pro Pro Ala Arg Pro Val Val Ser Cys Gln Ala Ala Asp
    110                 115                 120

TAT GAG AAC TTC TCT TGC ACT TGG AGT CCC AGC CAG ATC AGC GGT TTA      1153
Tyr Glu Asn Phe Ser Cys Thr Trp Ser Pro Ser Gln Ile Ser Gly Leu
125                 130                 135                 140

CCC ACC CGC TAC CTC ACC TCC TAC AGG AAG AAG ACA GTC CTA GGA GCT      1201
Pro Thr Arg Tyr Leu Thr Ser Tyr Arg Lys Lys Thr Val Leu Gly Ala
                145                 150                 155

GAT AGC CAG AGG AGG AGT CCA TCC ACA GGG CCC TGG CCA TGC CCA CAG      1249
Asp Ser Gln Arg Arg Ser Pro Ser Thr Gly Pro Trp Pro Cys Pro Gln
            160                 165                 170

GAT CCC CTA GGG GCT GCC CGC TGT GTT GTC CAC GGG GCT GAG TTC TGG      1297
Asp Pro Leu Gly Ala Ala Arg Cys Val Val His Gly Ala Glu Phe Trp
        175                 180                 185

AGC CAG TAC CGG ATT AAT GTG ACT GAG GTG AAC CCA CTG GGT GCC AGC      1345
Ser Gln Tyr Arg Ile Asn Val Thr Glu Val Asn Pro Leu Gly Ala Ser
    190                 195                 200

ACA CGC CTG CTG GAT GTG AGC TTG CAG AGC ATC TTG CGC CCT GAC CCA      1393
Thr Arg Leu Leu Asp Val Ser Leu Gln Ser Ile Leu Arg Pro Asp Pro
205                 210                 215                 220

CCC CAG GGC CTG CGG GTA GAG TCA GTA CCA GGT TAC CCC CGA CGC CTG      1441
Pro Gln Gly Leu Arg Val Glu Ser Val Pro Gly Tyr Pro Arg Arg Leu
                225                 230                 235

CGA GCC AGC TGG ACA TAC CCT GCC TCC TGG CCG TGC CAG CCC CAC TTC      1489
Arg Ala Ser Trp Thr Tyr Pro Ala Ser Trp Pro Cys Gln Pro His Phe
            240                 245                 250

CTG CTC AAG TTC CGT TTG CAG TAC CGT CCG GCG CAG CAT CCA GCC TGG      1537
Leu Leu Lys Phe Arg Leu Gln Tyr Arg Pro Ala Gln His Pro Ala Trp
        255                 260                 265

TCC ACG GTG GAG CCA GCT GGA CTG GAG GAG GTG ATC ACA GAT GCT GTG      1585
Ser Thr Val Glu Pro Ala Gly Leu Glu Glu Val Ile Thr Asp Ala Val
    270                 275                 280

GCT GGG CTG CCC CAT GCT GTA CGA GTC AGT GCC CGG GAC TTT CTA GAT      1633
Ala Gly Leu Pro His Ala Val Arg Val Ser Ala Arg Asp Phe Leu Asp
285                 290                 295                 300

GCT GGC ACC TGG AGC ACC TGG AGC CCG GAG GCC TGG GGA ACT CCG AGC      1681
Ala Gly Thr Trp Ser Thr Trp Ser Pro Glu Ala Trp Gly Thr Pro Ser
                305                 310                 315

ACT GGG ACC ATA CCA AAG GAG ATA CCA GCA TGG GGC CAG CTA CAC ACG      1729
Thr Gly Thr Ile Pro Lys Glu Ile Pro Ala Trp Gly Gln Leu His Thr
            320                 325                 330

CAG CCA GAG GTG GAG CCT CAG GTG GAC AGC CCT GCT CCT CCA AGG CCC      1777
Gln Pro Glu Val Glu Pro Gln Val Asp Ser Pro Ala Pro Pro Arg Pro
```

-continued

```
                335                 340                 345
TCC CTC CAA CCA CAC CCT CGG CTA CTT GAT CAC AGG GAC TCT GTG GAG      1825
Ser Leu Gln Pro His Pro Arg Leu Leu Asp His Arg Asp Ser Val Glu
    350                 355                 360

CAG GTA GCT GTG CTG GCG TCT TTG GGA ATC CTT TCT TTC CTG GGA CTG      1873
Gln Val Ala Val Leu Ala Ser Leu Gly Ile Leu Ser Phe Leu Gly Leu
365                 370                 375                 380

GTG GCT GGG GCC CTG GCA CTG GGG CTC TGG CTG AGG CTG AGA CGG GGT      1921
Val Ala Gly Ala Leu Ala Leu Gly Leu Trp Leu Arg Leu Arg Arg Gly
                385                 390                 395

GGG AAG GAT GGA TCC CCA AAG CCT GGG TTC TTG GCC TCA GTG ATT CCA      1969
Gly Lys Asp Gly Ser Pro Lys Pro Gly Phe Leu Ala Ser Val Ile Pro
            400                 405                 410

GTG GAC AGG CGT CCA GGA GCT CCA AAC CTG TAGAGGACCC AGGAGGGCTT        2019
Val Asp Arg Arg Pro Gly Ala Pro Asn Leu
            415                 420

CGGCAGATTC CACCTATAAT TCTGTCTTGC TGGTGTGGAT GGATGGACAG ATAGAAACCA    2079

GGCAGGACAG TAGATCCCTA TGGTTGGATC TCAGCTGGAA GTTCTGTTTG GAGCCCATTT    2139

CTGTGAGACC CTGTATTTCA AATTTGCAGC TGAAAGGTGC TTGTACCTCT GATTTCACCC    2199

CAGAGTTGGA GTTCTGCTCA AGGAACGTGT GTAATGTGTA CATCTGTGTC CATGTGTGAC    2259

CATGTGTCTG TGAGGCAGGG AACATGTATT CTCTGCATGC ATGTATGTAG GTGCCTGGGG    2319

AGTGTGTGTG GGTCCTTGGC TCTTGGCCTT TCCCCTTGCA GGGGTTGTGC AGGTGTGAAT    2379

AAAGAGAATA AGGAAGTTCT TGGAGATTAT ACTCAGAAAA AAAAAAAAA AGTCGACGCG     2439

GCCGCGAATT CCTGCAG                                                   2456

(2) INFORMATION FOR SEQ ID NO:2:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
                20                  25                  30

Pro Gly Val Gln Tyr Gly Gln Pro Gly Arg Ser Val Lys Leu Cys Cys
            35                  40                  45

Pro Gly Val Thr Ala Gly Asp Pro Val Ser Trp Phe Arg Asp Gly Glu
        50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140

Leu Thr Ser Tyr Arg Lys Lys Thr Val Leu Gly Ala Asp Ser Gln Arg
145                 150                 155                 160
```

```
Arg Ser Pro Ser Thr Gly Pro Trp Pro Cys Pro Gln Asp Pro Leu Gly
            165                 170                 175

Ala Ala Arg Cys Val Val His Gly Ala Glu Phe Trp Ser Gln Tyr Arg
        180                 185                 190

Ile Asn Val Thr Glu Val Asn Pro Leu Gly Ala Ser Thr Arg Leu Leu
            195                 200                 205

Asp Val Ser Leu Gln Ser Ile Leu Arg Pro Asp Pro Gln Gly Leu
        210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
                260                 265                 270

Pro Ala Gly Leu Glu Glu Val Ile Thr Asp Ala Val Ala Gly Leu Pro
                275                 280                 285

His Ala Val Arg Val Ser Ala Arg Asp Phe Leu Asp Ala Gly Thr Trp
            290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
                340                 345                 350

His Pro Arg Leu Leu Asp His Arg Asp Ser Val Glu Gln Val Ala Val
            355                 360                 365

Leu Ala Ser Leu Gly Ile Leu Ser Phe Leu Gly Leu Val Ala Gly Ala
        370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420
```

(2) INFORMATION FOR SEQ ID NO:3:

(i) SEQUENCE CHARACTERISTICS:
        (A) LENGTH: 1714 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 34..1359

(xi) SEQUENCE DESCRIPTION: SEQ ID NO:3:

```
TTCTTAGCCT GATAGGAGGA AGTCTTGGAG GCC ATG GCA CTC AGT CAC TGT GAT      54
                                 Met Ala Leu Ser His Cys Asp
                                  1               5

TAT CAA GAT GAG CAG CAG CTG CTC AGG GCT GAC CAG GGT CCT GGT GGC      102
Tyr Gln Asp Glu Gln Gln Leu Leu Arg Ala Asp Gln Gly Pro Gly Gly
        10                  15                  20
```

```
CGT GCT ACA GCC CTG GTG TCT TCC TCC TCC CCC TGC CCC CAA GCT TGG      150
Arg Ala Thr Ala Leu Val Ser Ser Ser Ser Pro Cys Pro Gln Ala Trp
 25                  30                  35

GGT CCT CCA GGG GTC CAG TAT GGA CAA CCT GGC AGG CCC GTG ATG CTG      198
Gly Pro Pro Gly Val Gln Tyr Gly Gln Pro Gly Arg Pro Val Met Leu
 40                  45                  50                  55

TGC TGC CCC GGA GTG AGT GCT GGG ACT CCA GTG TCC TGG TTT CGG GAT      246
Cys Cys Pro Gly Val Ser Ala Gly Thr Pro Val Ser Trp Phe Arg Asp
                 60                  65                  70

GGA GAT TCA AGG CTG CTC CAG GGA CCT GAC TCT GGG TTA GGA CAC AGA      294
Gly Asp Ser Arg Leu Leu Gln Gly Pro Asp Ser Gly Leu Gly His Arg
         75                  80                  85

CTG GTC TTG GCC CAG GTG GAC AGC CCT GAT GAA GGC ACT TAT GTC TGC      342
Leu Val Leu Ala Gln Val Asp Ser Pro Asp Glu Gly Thr Tyr Val Cys
             90                  95                 100

CAG ACC CTG GAT GGT GTA TCA GGG GGC ATG GTG ACC CTG AAG CTG GGC      390
Gln Thr Leu Asp Gly Val Ser Gly Gly Met Val Thr Leu Lys Leu Gly
                105                 110                 115

TTT CCC CCA GCA CGT CCT GAA GTC TCC TGC CAA GCG GTA GAC TAT GAA      438
Phe Pro Pro Ala Arg Pro Glu Val Ser Cys Gln Ala Val Asp Tyr Glu
120                 125                 130                 135

AAC TTC TCC TGT ACT TGG AGT CCA GGC CAG GTC AGC GGT TTG CCC ACC      486
Asn Phe Ser Cys Thr Trp Ser Pro Gly Gln Val Ser Gly Leu Pro Thr
                140                 145                 150

CGC TAC CTT ACT TCC TAC AGG AAG AAG ACG CTG CCA GGA GCT GAG AGT      534
Arg Tyr Leu Thr Ser Tyr Arg Lys Lys Thr Leu Pro Gly Ala Glu Ser
                155                 160                 165

CAG AGG GAA AGT CCA TCC ACC GGG CCT TGG CCG TGT CCA CAG GAC CCT      582
Gln Arg Glu Ser Pro Ser Thr Gly Pro Trp Pro Cys Pro Gln Asp Pro
        170                 175                 180

CTG GAG GCC TCC CGA TGT GTG GTC CAT GGG GCA GAG TTC TGG AGT GAG      630
Leu Glu Ala Ser Arg Cys Val Val His Gly Ala Glu Phe Trp Ser Glu
185                 190                 195

TAC CGG ATC AAT GTG ACC GAG GTG AAC CCA CTG GGT GCC AGC ACG TGC      678
Tyr Arg Ile Asn Val Thr Glu Val Asn Pro Leu Gly Ala Ser Thr Cys
200                 205                 210                 215

CTA CTG GAT GTG AGA TTA CAG AGC ATC TTG CGT CCT GAT CCA CCC CAA      726
Leu Leu Asp Val Arg Leu Gln Ser Ile Leu Arg Pro Asp Pro Pro Gln
                220                 225                 230

GGA CTG CGG GTG GAA TCC GTA CCT GGT TAC CCG AGA CGC CTG CAT GCC      774
Gly Leu Arg Val Glu Ser Val Pro Gly Tyr Pro Arg Arg Leu His Ala
            235                 240                 245

AGC TGG ACA TAC CCT GCC TCC TGG CGT CGC CAA CCC CAC TTT CTG CTC      822
Ser Trp Thr Tyr Pro Ala Ser Trp Arg Arg Gln Pro His Phe Leu Leu
        250                 255                 260

AAG TTC CGG TTG CAA TAC CGA CCA GCA CAG CAT CCA GCC TGG TCC ACG      870
Lys Phe Arg Leu Gln Tyr Arg Pro Ala Gln His Pro Ala Trp Ser Thr
265                 270                 275

GTG GAG CCC ATT GGC TTG GAG GAA GTG ATA ACA GAT GCT GTG GCT GGG      918
Val Glu Pro Ile Gly Leu Glu Glu Val Ile Thr Asp Ala Val Ala Gly
280                 285                 290                 295

CTG CCA CAC GCG GTA CGA GTC AGT GCC AGG GAC TTT CTG GAT GCT GGC      966
Leu Pro His Ala Val Arg Val Ser Ala Arg Asp Phe Leu Asp Ala Gly
                300                 305                 310

ACC TGG AGC GCC TGG AGC CCA GAG GCC TGG GGT ACT CCT AGC ACT GGT     1014
Thr Trp Ser Ala Trp Ser Pro Glu Ala Trp Gly Thr Pro Ser Thr Gly
            315                 320                 325

CCC CTG CAG GAT GAG ATA CCT GAT TGG AGC CAG GGA CAT GGA CAG CAG     1062
Pro Leu Gln Asp Glu Ile Pro Asp Trp Ser Gln Gly His Gly Gln Gln
        330                 335                 340
```

-continued

```
CTA GAG GCA GTA GTA GCT CAG GAG GAC AGC CCG GCT CCT GCA AGG CCT         1110
Leu Glu Ala Val Val Ala Gln Glu Asp Ser Pro Ala Pro Ala Arg Pro
    345                 350                 355

TCC TTG CAG CCG GAC CCA AGG CCA CTT GAT CAC AGG GAC CCC TTG GAG         1158
Ser Leu Gln Pro Asp Pro Arg Pro Leu Asp His Arg Asp Pro Leu Glu
360                 365                 370                 375

CAA GTA GCT GTG TTA GCG TCT CTG GGA ATC TTC TCT TGC CTT GGC CTG         1206
Gln Val Ala Val Leu Ala Ser Leu Gly Ile Phe Ser Cys Leu Gly Leu
                380                 385                 390

GCT GTT GGA GCT CTG GCA CTG GGG CTC TGG CTG AGG CTG AGA CGG AGT         1254
Ala Val Gly Ala Leu Ala Leu Gly Leu Trp Leu Arg Leu Arg Arg Ser
                395                 400                 405

GGG AAG GAT GGA CCG CAA AAA CCT GGG CTC TTG GCA CCC ATG ATC CCG         1302
Gly Lys Asp Gly Pro Gln Lys Pro Gly Leu Leu Ala Pro Met Ile Pro
                410                 415                 420

GTG GAA AAG CTT CCA GGA ATT CCA AAC CTG CAG AGG ACC CCA GAG AAC         1350
Val Glu Lys Leu Pro Gly Ile Pro Asn Leu Gln Arg Thr Pro Glu Asn
        425                 430                 435

TTC AGC TGATTTCATC TGTAACCCGG TCAGACTTGG GGTGGTTAAA AGGACAGGCA          1406
Phe Ser
440

GAAAGAGGCG GGGCAGTGGA TCCCTGTGGA TGGAGGTCTC AGCTGAAAGT CTGAGCTCTT       1466

TTCTTTGACA CCTATACTCC AAACTTGCTG CCGGCTGAAG GCTGTCTGGA CTTCCGATGT       1526

CCTGAGGTGG AAGTCCACCT GAGGAATGTG TACAGAAGTC TGTGTTCCTG TGATCGTGTG       1586

TGTATGTGAG ACAGGGAGCA AAAGTTCTCT GCATGTGTGT ACAGATGATT GGAGAGTGTG       1646

TGCGGTCTTG GGCTTGGCCC TTCTGGGAAG TGTGAAGAGT TGAAATAAAA GAGACGGAAG       1706

TTTTTGGA                                                                1714
```

(2) INFORMATION FOR SEQ ID NO:4:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Leu Ser His Cys Asp Tyr Gln Asp Glu Gln Gln Leu Leu Arg
1               5                   10                  15

Ala Asp Gln Gly Pro Gly Gly Arg Ala Thr Ala Leu Val Ser Ser Ser
                20                  25                  30

Ser Pro Cys Pro Gln Ala Trp Gly Pro Pro Gly Val Gln Tyr Gly Gln
            35                  40                  45

Pro Gly Arg Pro Val Met Leu Cys Cys Pro Gly Val Ser Ala Gly Thr
        50                  55                  60

Pro Val Ser Trp Phe Arg Asp Gly Asp Ser Arg Leu Leu Gln Gly Pro
65                  70                  75                  80

Asp Ser Gly Leu Gly His Arg Leu Val Leu Ala Gln Val Asp Ser Pro
                85                  90                  95

Asp Glu Gly Thr Tyr Val Cys Gln Thr Leu Asp Gly Val Ser Gly Gly
                100                 105                 110

Met Val Thr Leu Lys Leu Gly Phe Pro Pro Ala Arg Pro Glu Val Ser
            115                 120                 125

Cys Gln Ala Val Asp Tyr Glu Asn Phe Ser Cys Thr Trp Ser Pro Gly
        130                 135                 140
```

-continued

```
Gln Val Ser Gly Leu Pro Thr Arg Tyr Leu Thr Ser Tyr Arg Lys Lys
145                 150                 155                 160

Thr Leu Pro Gly Ala Glu Ser Gln Arg Glu Ser Pro Ser Thr Gly Pro
                 165                 170                 175

Trp Pro Cys Pro Gln Asp Pro Leu Glu Ala Ser Arg Cys Val Val His
             180                 185                 190

Gly Ala Glu Phe Trp Ser Glu Tyr Arg Ile Asn Val Thr Glu Val Asn
         195                 200                 205

Pro Leu Gly Ala Ser Thr Cys Leu Leu Asp Val Arg Leu Gln Ser Ile
    210                 215                 220

Leu Arg Pro Asp Pro Gln Gly Leu Arg Val Glu Ser Val Pro Gly
225                 230                 235                 240

Tyr Pro Arg Arg Leu His Ala Ser Trp Thr Tyr Pro Ala Ser Trp Arg
                245                 250                 255

Arg Gln Pro His Phe Leu Leu Lys Phe Arg Leu Gln Tyr Arg Pro Ala
            260                 265                 270

Gln His Pro Ala Trp Ser Thr Val Glu Pro Ile Gly Leu Glu Glu Val
        275                 280                 285

Ile Thr Asp Ala Val Ala Gly Leu Pro His Ala Val Arg Val Ser Ala
    290                 295                 300

Arg Asp Phe Leu Asp Ala Gly Thr Trp Ser Ala Trp Ser Pro Glu Ala
305                 310                 315                 320

Trp Gly Thr Pro Ser Thr Gly Pro Leu Gln Asp Glu Ile Pro Asp Trp
                325                 330                 335

Ser Gln Gly His Gly Gln Gln Leu Glu Ala Val Val Ala Gln Glu Asp
            340                 345                 350

Ser Pro Ala Pro Ala Arg Pro Ser Leu Gln Pro Asp Pro Arg Pro Leu
        355                 360                 365

Asp His Arg Asp Pro Leu Glu Gln Val Ala Val Leu Ala Ser Leu Gly
    370                 375                 380

Ile Phe Ser Cys Leu Gly Leu Ala Val Gly Ala Leu Ala Leu Gly Leu
385                 390                 395                 400

Trp Leu Arg Leu Arg Arg Ser Gly Lys Asp Gly Pro Gln Lys Pro Gly
                405                 410                 415

Leu Leu Ala Pro Met Ile Pro Val Glu Lys Leu Pro Gly Ile Pro Asn
            420                 425                 430

Leu Gln Arg Thr Pro Glu Asn Phe Ser
        435                 440
```

HUMAN INTERLEUKIN-11 RECEPTOR

This application is a division of application Ser. No. 08/663,584, filed Jun. 14, 1996 which is a C-I-P of application Ser. No. 08/362,304, filed Dec. 22, 1994, now abandoned.

FIELD OF THE INVENTION

The present invention relates to the human interleukin-11 receptor, fragments thereof and recombinant polynucleotides and cells useful for expressing such proteins.

BACKGROUND OF THE INVENTION

A variety of regulatory molecules, known as cytokines, have been identified including interleukin-11 (IL-11). The various protein forms of IL-11 and DNA encoding various forms of IL-11 activity are described in Bennett, et al., U.S. Pat. No. 5,215,895 (Jun. 1, 1993); McCoy, et al, U.S. Pat. No. 5,270,181 (Dec. 14, 1993); and McCoy, et al., U.S. Pat. No. 5,292,646 (Mar. 8, 1994), all incorporated herein by reference. Thus, the term "IL-11" includes proteins having the biological activity described in these patents, whether produced by recombinant genetic engineering techniques; purified from cell sources producing the factor naturally or upon induction with other factors; or synthesized by chemical techniques; or a combination of the foregoing.

IL-11 is a pleiotropic cytokine that has been implicated in production of several biological activities including: induction of multipotential hematopoietic progenitor cell proliferation (Musashi et al. (1991) Blood, 78, 1448–1451); enhancement of megakaryocyte and platelet formation (Burstein et al. (1992) J. Cell. Physiol., 153, 305–312); stimulation of acute phase protein synthesis (Baumann et al. (1991) J. Biol. Chem., 266, 20424–20427); inhibition of adipocyte lipoprotein lipase activity (Kawashima et al. (1991) FEBS Lett., 283, 199–202); and effects on neurotransmitter phenotype (Fann et al. (1994) Proc. Natl. Acad. Sci. USA, 91, 43–47).

IL-11 may be used in a pharmaceutical preparation or formulation to treat immune deficiencies, specifically deficiencies in hematopoietic progenitor cells, or disorders relating thereto. Treatment of the other disorders or stimulation of the immune systems of cells thereof may also employ IL-11. IL-11 may also be employed in methods for treating cancer and other disease. Such pathological states may result from disease, exposure to radiation or drugs, and include, for example, leukopenia, bacterial and viral infections, anemia, B cell or T cell deficiencies such as immune cell or hematopoietic cell deficiency following a bone marrow transplantation. IL-11 may also be used to potentiate the immune response to a variety of vaccines creating longer lasting and more effective immunity. Therapeutic treatment of cancer and other diseases with IL-11 may avoid undesirable side effects caused by treatment with presently available drugs.

Like most cytokines, IL-11 exhibits certain biological activities by interacting with an IL-11 receptor (IL-11R) on the surface of target cells. It would be desirable to identify and clone the sequence for the human receptor so that IL-11R proteins can be produced for various reasons, including production of therapeutics and screening for inhibitors of IL-11 binding to the receptor and receptor signalling.

SUMMARY OF THE INVENTION

In accordance with the present invention, polynucleotides encoding the human interleukin-11 receptor are disclosed. In certain embodiments, the invention provides an isolated polynucleotide comprising a nucleotide sequence selected from the group consisting of:

(a) the nucleotide sequence of SEQ ID NO:1 from nucleotide 803 to nucleotide 1999;

(b) a nucleotide sequence varying from the sequence of the nucleotide sequence specified in (a) as a result of degeneracy of the genetic code;

(c) an allelic variant of the nucleotide sequence specified in (a); and (d) a fragment of (a) or (b) encoding a protein having the ability to bind IL-11.

Preferably, the nucleotide sequence encodes a protein having a biological activity of the human IL-11 receptor. The nucleotide sequence may be operably linked to an expression control sequence. In preferred embodiments, the polynucleotide comprises the nucleotide sequence of SEQ ID NO:1 from nucleotide 803 to nucleotide 1999 or a fragment thereof; the nucleotide sequence of SEQ ID NO:1 from nucleotide 803 to nucleotide 1828 or a fragment thereof; the nucleotide sequence of SEQ ID NO:1 from nucleotide 1904 to nucleotide 1999 or a fragment thereof; the nucleotide sequence of SEQ ID NO:1 from nucleotide 734 to nucleotide 1999 or a fragment thereof; the nucleotide sequence of SEQ ID NO:1 from nucleotide 1067 to nucleotide 1828 or a fragment thereof; or the nucleotide sequence of SEQ ID NO:1 from nucleotide 1067 to nucleotide 1999 or a fragment thereof. Other preferred embodiments include the nucleotide sequence of SEQ ID NO:1 from nucleotide 734 to nucleotide 1828; the nucleotide sequence of SEQ ID NO:1 from nucleotide 734 to nucleotide 1810; the nucleotide sequence of SEQ ID NO:1 from nucleotide 734 to nucleotide 1768; and the nucleotide sequence of SEQ ID NO:1 from nucleotide 734 to nucleotide 1705. In other embodiments, the polynucleotide comprises a nucleotide sequence capable of hybridizing to the nucleotides sequence of SEQ ID NO:1 under highly stringent conditions.

The invention also provides isolated polynucleotides comprising a nucleotide sequence encoding a peptide or protein comprising an amino acid sequence selected from the group consisting of:

(a) the amino acid sequence of SEQ ID NO:2;

(b) the amino acid sequence of SEQ ID NO:2 from amino acids 24 to 422;

(c) the amino acid sequence of SEQ ID NO:2 from amino acids 24 to 365;

(d) the amino acid sequence of SEQ ID NO:2 from amino acids 391 to 422;

(e) the amino acid sequence of SEQ ID NO:2 from amino acids 112 to 422;

(f) the amino acid sequence of SEQ ID NO: 2 from amino acids 112 to 365; and (g) fragments of (a)–(f) having a biological activity of the human IL-11 receptor.

Host cells, preferably mammalian cells, transformed with the polynucleotides are also provided.

In other embodiments, the invention provides a process for producing a human IL-11R protein. The process comprises:

(a) growing a culture of the host cell of the present invention in a suitable culture medium; and (b) purifying the human IL-11R protein from the culture. Proteins produced according to these methods are also provided.

The present invention also provides for an isolated human IL-11R protein comprising an amino acid sequence selected from the group consisting of:

(a) the amino acid sequence of SEQ ID NO:2;
(b) the amino acid sequence of SEQ ID NO:2 from amino acids 24 to 422;
(c) the amino acid sequence of SEQ ID NO:2 from amino acids 24 to 365;
(d) the amino acid sequence of SEQ ID NO:2 from amino acids 391 to 422;
(e) the amino acid sequence of SEQ ID NO:2 from amino acids 112 to 422;
(f) the amino acid sequence of SEQ ID NO:2 from amino acids 112 to 365;
(g) the amino acid sequence of SEQ ID NO:2 from amino acids 24 to 359;
(h) the amino acid sequence of SEQ ID NO:2 from amino acids 24 to 345;
(i) the amino acid sequence of SEQ ID NO:2 from amino acids 24 to 324; and
(j) fragments of (a)–(i) having a biological activity of the human IL-11 receptor. Preferably the protein comprises the amino acid sequence of SEQ ID NO:2; the sequence from amino acid 24 to 422 of SEQ ID NO:2; the sequence from amino acid 24 to 365 of SEQ ID NO:2; or the sequence from amino acid 391 to 422 of SEQ ID NO:2. In other preferred embodiments the protein comprises an amino acid sequence beginning with amino acid 23 or amino acid 26 of SEQ ID NO:2. Pharmaceutical compositions comprising a protein of the present invention and a pharmaceutically acceptable carrier are also provided.

The present invention further provides for compositions comprising an antibody which specifically reacts with a protein of the present invention.

Methods of identifying an inhibitor of IL-11 binding to the human IL-11 receptor are also provided. These methods comprise:

(a) combining a human IL-11R protein or a fragment thereof with IL-11 or a fragment thereof, said combination forming a first binding mixture;
(b) measuring the amount of binding between the protein and the IL-11 or fragment in the first binding mixture;
(c) combining a compound with the protein and the IL-11 or fragment to form a second binding mixture;
(d) measuring the amount of binding in the second binding mixture; and
(e) comparing the amount of binding in the first binding mixture with the amount of binding in the second binding mixture;

wherein the compound is capable of inhibiting IL-11 binding to the human IL-11 receptor when a decrease in the amount of binding of the second binding mixture occurs. Optionally, the first and/or second binding mixture may further comprise gp130 or a fragment thereof capable of binding to the protein of claim 11 or the IL-11 or fragment used therein. Inhibitors of IL-11R identified by these methods and pharmaceutical compositions containing them are also provided.

Methods of inhibiting binding of IL-11 to the human IL-11 receptor in a mammalian subject are also disclosed which comprise administering a therapeutically effective amount of a composition containing a human IL-11R protein, an IL-11R inhibitor or an antibody to a human IL-11R protein. Methods of treating or preventing loss of bone mass in a mammalian subject using these compositions are also provided.

In yet other embodiments the invention provides for an isolated polynucleotide comprising a nucleotide sequence encoding a peptide or protein comprising an amino acid sequence selected from the group consisting of:

(a) the amino acid sequence of SEQ ID NO:2;
(b) the amino acid sequence of SEQ ID NO:2 from amino acids 24 to 422;
(c) the amino acid sequence of SEQ ID NO:2 from amino acids 24 to 365;
(d) the amino acid sequence of SEQ ID NO:2 from amino acids 391 to 422;
(e) the amino acid sequence of SEQ ID NO:2 from amino acids 112 to 422;
(f) the amino acid sequence of SEQ ID NO:2 from amino acids 112 to 365;
(g) the amino acid sequence of SEQ ID NO:2 from amino acids 24 to 359;
(h) the amino acid sequence of SEQ ID NO:2 from amino acids 24 to 345;
(i) the amino acid sequence of SEQ ID NO:2 from amino acids 24 to 324; and
(j) fragments of (a)–(i) having a biological activity of the human IL-11 receptor.

DETAILED DESCRIPTION OF PREFERRED EMBODIMENTS

Figure 1:
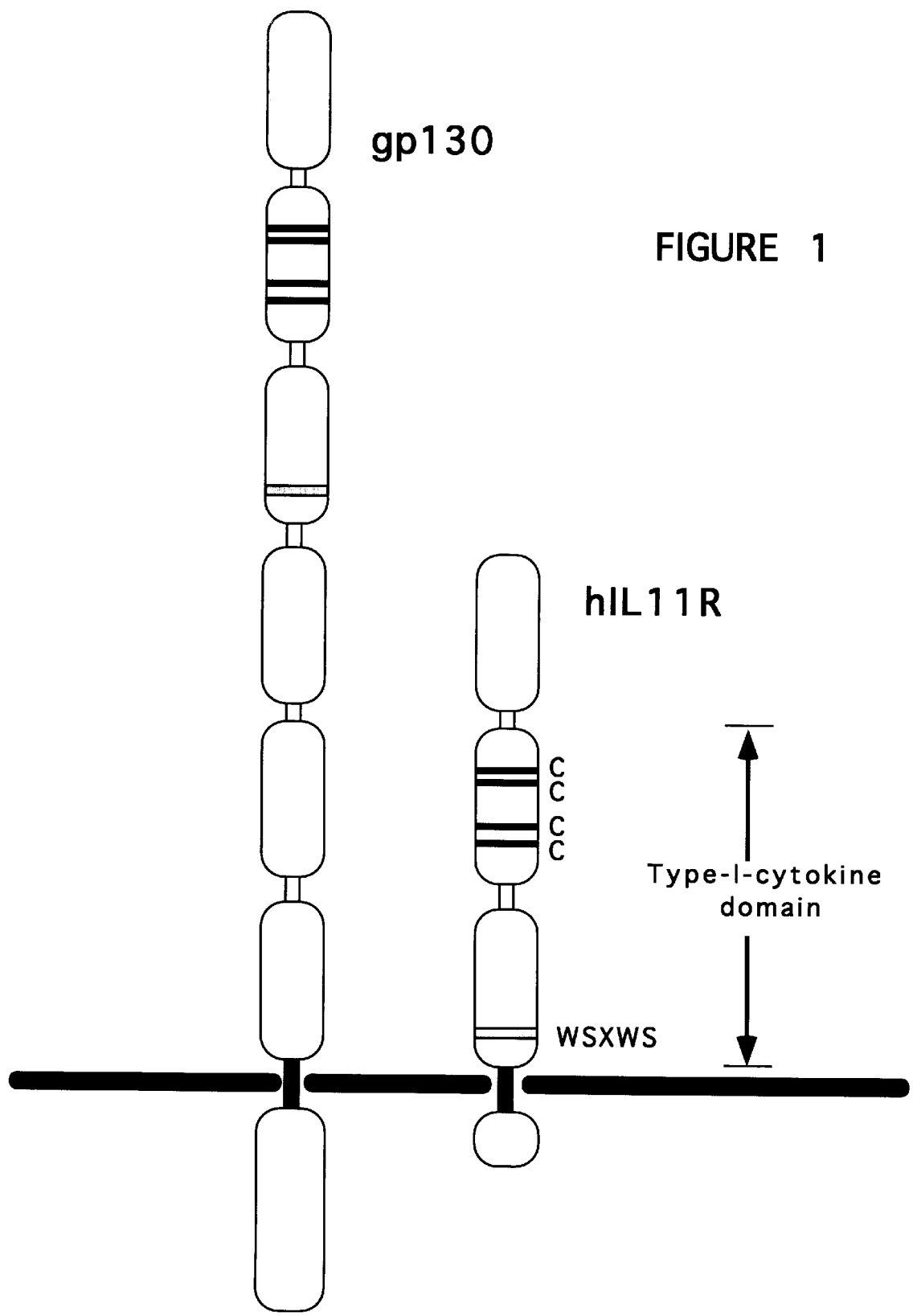
FIG. 1 depicts a schematic representation of the structures of the human IL-11 receptor and gp130.

The inventors of the present application have for the first time identified and provided a polynucleotide encoding the human IL-11 receptor (human IL-11R).

SEQ ID NO:1 provides the nucleotide sequence of a cDNA encoding the human IL-11R. SEQ ID NO:2 provides the amino acid sequence of the receptor, included a putative signal sequence from amino acids 1–23. The mature human IL-11R is believed to have the sequence of amino acids 23–422, 24–422 or 26–422 of SEQ ID NO:2. Applicants have found that upon expression human IL-11R proteins are found to have N-termini at either amino acid 23 (approximately 20%), 24 (approximately 24%) or 26 (approximately 50%). References herein to the "mature" form of the protein are intended to refer to forms beginning with any of these amino acids, and are sometimes references herein as having the sequence "23/24/26–422" of SEQ ID NO:2.

The mature receptor has at least three distinct domains: an extracellular domain (comprising approximately amino acids 23/24/26–365 of SEQ ID NO:2), a transmembrane domain (comprising approximately amino acids 366–390 of SEQ ID NO:2) and an intracellular domain (comprising approximately amino acids 391–422 of SEQ ID NO:2). The extracellular domain is further divided into an immunoglobulin-like domain (comprising approximately amino acids 23/24/26–111 of SEQ ID NO:2) and a type-I-cytokine domain (comprising approximately amino acids 112–365 of SEQ ID NO:2).

Soluble forms of human IL-11R protein can also be produced. Such soluble forms include without limitation proteins comprising amino acids 1–365 and 23/24/26–365 of SEQ ID NO:2. The soluble forms of the human IL-11R are further characterized by being soluble in aqueous solution, preferably at room temperature. Human IL-11R proteins comprising only the intracellular domain or a portion thereof may also be produced. Any forms of human IL-11R of less than full length are encompassed within the present invention and are referred to herein collectively as "human IL-11R" or "human IL-11R proteins." Human IL-11R proteins of less than full length may be produced by expressing a corresponding fragment of the polynucleotide encoding the full-length human IL-11R protein (SEQ ID NO:1). These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

Based upon similarity to the structure of the IL-6 receptor, it is predicted that IL-11R proteins containing only the type-I cytokine domain of the extracellular region of the full length receptor will be capable of binding IL-11 and inducing receptor signalling. As a result, IL-11R proteins comprising amino acids 112 to 365 of SEQ ID NO:2, IL-11R proteins comprising amino acids 112 to 390 of SEQ ID NO:2, and IL-11R proteins comprising amino acids 112 to 422 of SEQ ID NO:2 are provided by the present invention. Polynucleotides encoding such proteins (such as for example a polynucleotide comprising the nucleotides sequence of SEQ ID NO:1 from nucleotide 1067 to nucleotide 1828, a polynucleotide comprising the nucleotides sequence of SEQ ID NO:1 from nucleotide 1067 to nucleotide 1906, and a polynucleotide comprising the nucleotides sequence of SEQ ID NO:1 from nucleotide 1067 to nucleotide 1999, respectively) are also provided by the invention. For the purposes of the present invention, a protein has "a biological activity of the human IL-11 receptor" if it possess one or more of the following characteristics: (1) the ability to bind IL-11 or a fragment thereof (preferably a biologically active fragment thereof); (2) the ability to bind to cytosolic proteins or molecules involved in the signalling pathway invoked by IL-11 binding to human IL-11R; (3) the ability to produce a signal characteristic of the binding of IL-11 to human IL-11R (where the protein in question either contains a portion able to bind IL-11 or where the protein in question would produce such signal if joined to another protein which is able to bind IL-11); (4) the ability to bind to gp130 or a fragment thereof (either in the presence or absence of IL-11); (5) the ability to induce tyrosine phosphorylation of gp130; (6) the ability to induce tyrosine phosphorylation of JAK kinases; or (7) the ability to induce tyrosine phosphorylation of the STAT family of DNA binding proteins (Zhong et al. (1994) Science 264, 95–98). Preferably, the biological activity possessed by the protein is the ability to bind IL-11 or a fragment hereof, more prefereably with a $K_D$ of about 0.1 to about 100 nM, most preferably with a $K_D$ of about 1 to about 10 nM.

Human IL-11R or active fragments thereof (human IL-11R proteins) may be fused to carrier molecules such as immunoglobulins. For example, soluble forms of the human IL-11R may be fused through "linker" sequences to the Fc portion of an immunoglobulin. Other fusions proteins, such as those with GST, Lex-A or MBP, may also be used.

The invention also encompasses allelic variations of the nucleotide sequence as set forth in SEQ ID NO:1, that is, naturally-occurring alternative forms of the isolated polynucleotide of SEQ ID NO:1 which also encode human IL-11R proteins, preferably those proteins having a biological activity of human IL-11R. Also included in the invention are isolated polynucleotides which hybridize to the nucleotide sequence set forth in SEQ ID NO:1 under highly stringent conditions (for example, 0.1×SSC at 65° C.). Isolated polynucleotides which encode human IL11R proteins but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications are also included in the invention.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the human IL-11R protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the human IL-11R protein is expressed by a host cell which has been transformed (transfected) with the ligated polynucleotide/expression control sequence.

A number of types of cells may act as suitable host cells for expression of the human IL-11R protein. Any cell type capable of expressing functional human IL-11R protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The human IL-11R protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin* No. 1555 (1987), incorporated herein by reference. Soluble forms of the human IL-11R protein may also be produced in insect cells using appropriate isolated polynucleotides as described above.

Alternatively, the human IL-11R protein may be produced in lower eukaryotes such as yeast or in prokaryotes such as bacteria. Suitable yeast strains include *Saccharomyces cerevisiae, Schizosaccharomyces pombe*, Kluyveromyces strains, Candida, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, *Meth. Enzym.*, 185:187–195 (1990). EP 0433225 and copending application U.S. Ser. No. 08/163, 877 describe other appropriate methods.

The human IL-11R protein of the invention may also be expressed as a product of transgenic animals, e.g., as a component of the milk of transgenic cows, goats, pigs, or sheep which are characterized by somatic or germ cells containing a polynucleotide sequence encoding the human IL-11R protein.

The human IL-11R protein of the invention may be prepared by growing a culture transformed host cells under culture conditions necessary to express the desired protein. The resulting expressed protein may then be purified from the culture medium or cell extracts. Soluble forms of the human IL-11R protein of the invention can be purified from conditioned media. Membrane-bound forms of human IL-11R protein of the invention can be purified by preparing a total membrane fraction from the expressing cell and extracting the membranes with a non-ionic detergent such as Triton X-100.

The human IL-11R protein can be purified using methods known to those skilled in the art. For example, the human IL-11R protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the human IL-11R protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the human IL-11R protein. Affinity columns including IL-11 or fragments thereof or including antibodies to the IL-11R protein can also be used in purification in accordance with known methods. Some or all of the foregoing purification steps, in various combinations or with other known methods, can also be employed to provide a substantially purified isolated recombinant protein. Preferably, the isolated human IL-11R protein is purified so that it is substantially free of other mammalian proteins.

Human IL-11R proteins of the invention may also be used to screen for agents which are capable of binding to human IL-11R or interfere with the binding of IL-11 to the human IL-11R (either the extracellular or intracellular domains) and thus may act as inhibitors of normal binding and cytokine action (IL-11R inhibitors). Binding assays using a desired binding protein, immobilized or not, are well known in the art and may be used for this purpose using the human IL-11R protein of the invention. Purified cell based or protein based (cell free) screening assays may be used to identify such agents. For example, human IL-11R protein may be immobilized in purified form on a carrier and binding to purified human IL-11R protein may be measured in the presence and in the absence of potential inhibiting agents. A suitable binding assay may alternatively employ a soluble form of human IL-11R of the invention.

In such a screening assay, a first binding mixture is formed by combining IL-11 or a fragment thereof and human IL-11R protein, and the amount of binding in the first binding mixture ($B_0$) is measured. A second binding mixture is also formed by combining IL-11 or a fragment thereof, human IL-11R protein, and the compound or agent to be screened, and the amount of binding in the second binding mixture (B) is measured. The amounts of binding in the first and second binding mixtures are compared, for example, by performing a calculation of the ratio $B/B_0$. A compound or agent is considered to be capable of inhibiting binding if a decrease in binding in the second binding mixture as compared to the first binding mixture is observed. Optionally, gp130 can be added to one or both of the binding mixtures. The formulation and optimization of binding mixtures is within the level of skill in the art, such binding mixtures may also contain buffers and salts necessary to enhance or to optimize binding, and additional control assays may be included in the screening assay of the invention.

Compounds found to reduce the binding activity of human IL-11R protein to IL-11 or its fragment to any degree, preferably by at least about 10%, more preferably greater than about 50% or more, may thus be identified and then secondarily screened in other binding assays and in vivo assays. By these means compounds having inhibitory activity for IL-11R binding which may be suitable as therapeutic agents may be identified.

Human IL-11R proteins, and polynucleotides encoding them, may also be used as diagnostic agents for detecting the expression or presence of IL-11R, IL-11 or cells expressing IL-11R or IL-11. The proteins or polynucleotides may be employed for such purpose in standard procedures for diagnostics assays using these types of materials. Suitable methods are well known to those skilled in the art.

Human IL-11R acts as a mediator of the known biological activities of IL-11. As a result, isolated human IL-11R protein and IL-11R inhibitors may be useful in treatment or modulation of various medical conditions in which IL-11 is implicated or which are effected by the activity (or lack thereof) of IL-11 (collectively "IL-11-related conditions"). IL-11-related conditions include without limitation immune deficiencies, specifically deficiencies in hematopoietic progenitor cells, or disorders relating thereto, cancer and other disease. Such pathological states may result from disease, exposure to radiation or drugs, and include, for example, leukopenia, bacterial and viral infections, anemia, B cell or T cell deficiencies such as immune cell or hematopoietic cell deficiency following a bone marrow transplantation.

It is also believed that IL-11 and IL-11R may play a role in the regulation of bone maturation and repair (Girasole et al. (1994) J. Clin. Invest. 93, 1516–1524; Passeri et al. (1992) J. Bone Miner. Res., 7(S1), S110 Abst.; Passeri et al.

(1993) J. Bone Miner. Res., 8(S1), S162 Abst. ). As a result, human IL-11R protein and IL-11R inhibitors may be useful in treatment of bone loss (including that associated with osteoporosis, post-menopausal osteoporosis, senile osteoporosis, idiopathic osteoporosis, Pagets disease, multipe myeloma, and hypogonadal conditions).

Human IL-11R protein and IL-11R inhibitors, purified from cells or recombinantly produced, may be used as a pharmaceutical composition when combined with a pharmaceutically acceptable carrier. Such a composition may contain, in addition to human IL-11R or ligand and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-15, G-CSF, stem cell factor, and erythropoietin. The pharmaceutical composition may contain thrombolytic or anti-thrombotic factors such as plasminogen activator and Factor VII. The pharmaceutical composition may further contain other anti-inflammatory agents. Such additional factors and/ or agents may be included in the pharmaceutical composition to produce a synergistic effect with isolated human IL-11R protein or IL-11R inhibitor, or to minimize side effects caused by the isolated human IL-11R or IL-11R inhibitor. Conversely, isolated human IL-11R or IL-11R inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated human IL-11R protein or IL-11R inhibitor is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated human IL-11R protein or IL-11R inhibitor is administered to a mammal. Isolated human IL-11R protein or IL-11R inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, human IL-11R protein or IL-11R inhibitor may be administered either simultaneously with the cytokine (s), lymphokine(s), other hematopoietic factor(s), thrombolytic or anti-thrombotic factors, or sequentially. If administered sequentially, the attending physician will decide on the appropriate sequence of administering human IL-11R protein or IL-11R inhibitor in combination with cytokine(s), lymphokine(s), other hematopoietic factor(s), thrombolytic or anti-thrombotic factors.

Administration of human IL-11R protein or IL-11R inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of human IL-11R protein or IL-11R inhibitor is administered orally, human IL-11R protein or IL-11R inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% human IL-11R protein or IL-11R inhibitor, and preferably from about 25 to 90% human IL-11R protein or IL-11R inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of human IL-11R protein or IL-11R inhibitor, and preferably from about 1 to 50% human IL-11R protein or IL-11R inhibitor.

When a therapeutically effective amount of human IL-11R protein or IL-11R inhibitor is administered by intravenous, cutaneous or subcutaneous injection, human IL-11R protein or IL-11R inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to human IL-11R protein or IL-11R inhibitor an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of human IL-11R protein or IL-11R inhibitor in the pharmaceutical composition of the present invention will depend upon the nature and severity of the condition being treated, and on the nature of prior treatments which the patient has undergone. Ultimately, the attending physician will decide the amount of human IL-11R protein or IL-11R inhibitor with which to treat each individual patient. Initially, the attending physician will administer low doses of human IL-11R protein or IL-11R inhibitor and observe the patient's response. Larger doses of human IL-11R protein or IL-11R inhibitor may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of human IL-11R protein or IL-11R inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the human IL-11R protein or IL-11R inhibitor will be in the range of 12 to 24 hours of continuous intravenous administration. Ultimately the attending physician will decide on the appropriate duration of intravenous therapy using the pharmaceutical composition of the present invention.

Human IL-11R proteins of the invention may also be used to immunize animals to obtain polyclonal and monoclonal antibodies which specifically react with the human IL-11R protein and which may inhibit binding of IL-11 or fragments thereof to the receptor. Such antibodies may be obtained using the entire human IL-11R as an immunogen, or by using fragments of human IL-11R, such as the soluble mature human IL-11R. Smaller fragments of the human IL-11R may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J.Amer.Chem.Soc. 85, 2149–2154 (1963); J. L. Krstenansky, et al., FEBS Lett. 211, 10 (1987).

Neutralizing or non-neutralizing antibodies (preferably monoclonal antibodies) binding to human IL-11R protein may also be useful therapeutics for certain tumors and also in the treatment of conditions described above. These neutralizing monoclonal antibodies may be capable of blocking IL-11 binding to the human IL-11R.

EXAMPLE 1

Isolation of Human IL-11R cDNA

Generation of DNA Probes:

DNA probes derived from the murine Etl-2 sequence (SEQ ID NO:3) were obtained by PCR from murine placenta cDNA. The amino terminal probe corresponds to base pairs 418–570 and the carboxy terminal probe to base pairs 847–1038 of the murine Etl-2 sequence. The DNA probes were gel purified and radiolabeled using α32P-dATP and α32P-dCTP.

cDNA Library Screening:

cDNA was generated from activated human PBMC using the Superscript Choice System and cloned into the EcoR1 site of ZAP II (Stratagene). The resulting phage were used to infect E. coli strain BB4. One million phage were plated on 150 mm NZCYM plates at a density of 15000 pfu/plate. Plaques were transferred to duplicate Duralose nitrocellulose filters (Stratagene). Following alkali denaturation and heat fixation the filters were pre-hybridized in 5× SSC, 5× Denhardts, 0.1% SDS, and 50 µg/ml yeast tRNA for 2 hours at 65° C. One set of filters was hybridized with the amino-terminal probe and the other set with the carboxy-terminal probe ($5 \times 10^5$ cpm/ml) for 48 hrs at 55° C. in pre-hybridization buffer. The filters were washed with 4× SSC, 0.1% SDS once at 25° C. and twice at 55° C. Plaques that hybridized to both probes were identified by autoradiography.

Of the one million plaques screened two plaques hybridized to both of the probes. These plaques were picked and the phage eluted into SM media containing chloroform. The resulting phage were used to reinfect E. coli strain BB4 and plated on NZCYM plates at a density of 100–300 pfu/plate for a secondary screen.

Following the secondary screen plasmid DNA was isolated from the ZAPII plaques by excision using helper phage (Stratagene). The DNA sequence of the inserts was determined on an Applied Biosystems DNA sequencer.

Clone phIL11R14-2 containing the polynucleotide having the sequence of SEQ ID NO:1 was deposited with ATCC at accession number 69731 on Dec. 22, 1994.

EXAMPLE 2

Expression of Soluble Human IL-11R Protein and Assay of Activity

A soluble form of human IL-11R protein was expressed in mammalian cells. The expresssed recombinant protein was capable of transducing a signal in BAF130-9 cells.

Figure 2:
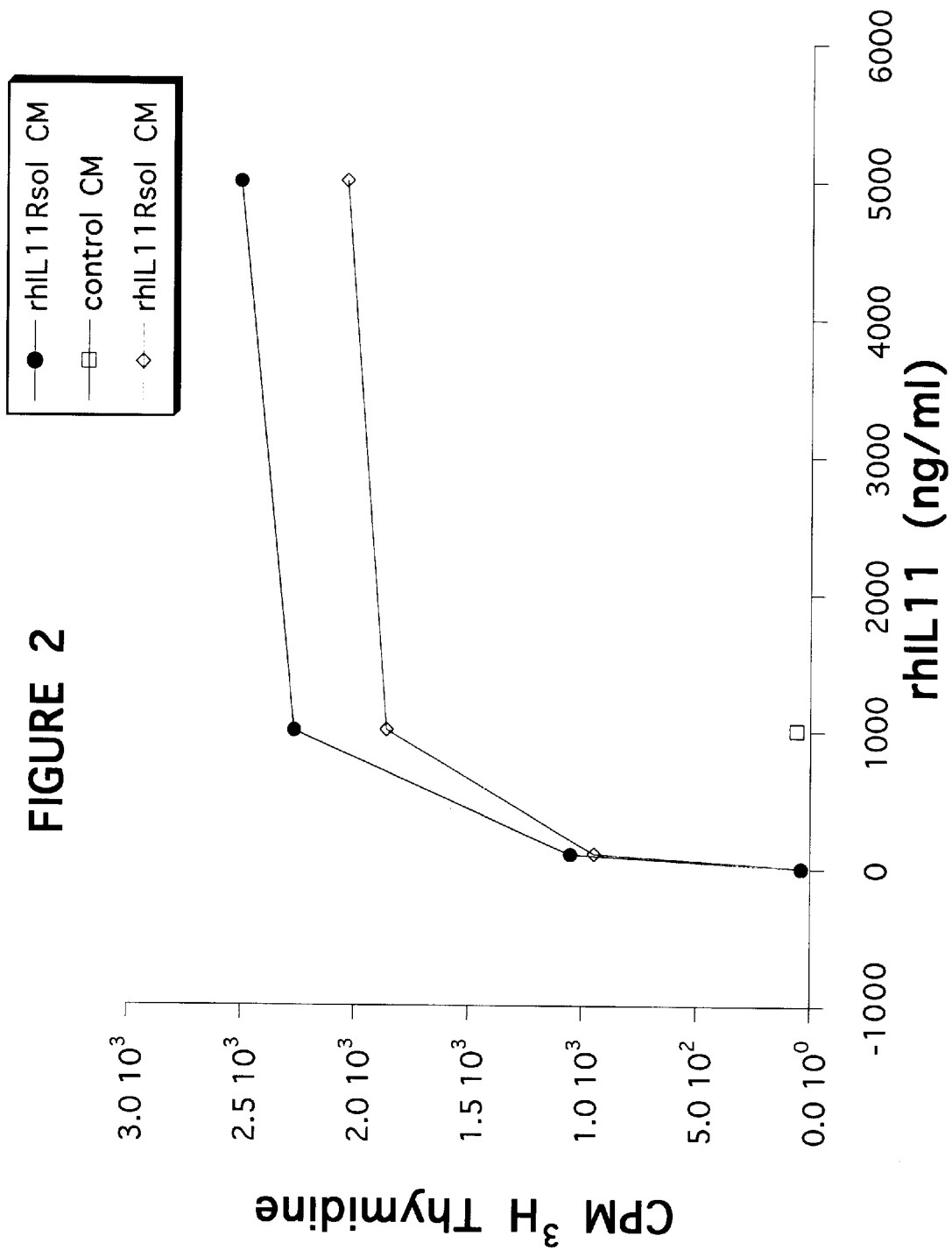
FIG. 2 presents data demonstrating the biological activity of a soluble form of recombinant human IL-11R protein.

A portion of the full length human IL-11R sequence (nucleotides 734–1828 of SEQ ID NO:1 encoding amino acids 1–365 of SEQ ID NO:2) corresponding to a soluble form was cloned into the mammalian expression vector pED and used to transfect COSM6 cells. 40 hours after transfection conditioned media was removed, concentrated 5 fold and used in proliferation assays with the murine cell line BAF130-9 (Hibi, M. et al. (1990) Cell 63, 1149–57), a derivative of the BAFB03 cell line expressing the human gp130 signal transducer. BAF130-9 cells do not proliferate in response to IL-11 or IL-6 alone, but do proliferate in response to a combination of IL-6 and soluble IL-6R (Hibi et al., supra). BAF130-9 cells ($1 \times 10^4$ cell in 0.1 ml) were cultured in RPMI 1640 medium/10% FCS with increasing concentrations of recombinant human IL-11 in the absence or presence of 10 µl of conditioned media from mock transfected cells or cells transfected with the soluble human IL-11R sequence. After forty hours the cells were pulse-labeled with $^3$H-thymidine (0.5 µCi/well) for eight hours and incorporated nucleotide was determined. As shown in FIG. 2, BAF130-9 cells do not proliferate in response to IL-11 or soluble IL-11R alone, but do proliferate in the presence of both IL-11 and soluble IL-11R.

Other human IL-11R proteins can be tested in this model to determine whether they exhibit a "biological activity" of human IL-11R as defined herein.

EXAMPLE 3

Other Systems for Determination Biological Activity of Human IL-11R Protein

Other systems can be used to determine whether a specific human IL-11R protein exhibits a "biological activity" of human IL-11R as defined herein. The following are examples of such systems.

Assays for IL-11 Binding

The ability of a human IL-11R protein to bind IL-11 or a fragment thereof can be determine by any sutiable assays which can detect such binding. Some suitable examples follow.

Binding of IL-11 to the extracellular region of the human IL-11R protein will specifically cause a rapid induction of phosphotyrosine on the receptor protein. Assays for ligand binding activity as measured by induction of phosphorylation are described below.

Alternatively, a human IL-11R protein (such as, for example, a soluble form of the extracellular domain) is produced and used to detect IL-11 binding. For example, a DNA construct is prepared in which the extracellular domain (truncated prior, preferably immediately prior, to the predicted transmembrane domain) is ligated in frame to a cDNA encoding the hinge $C_H2$ and $C_H3$ domains of a human immunoglobulin (Ig) γ1. This construct is generated in an appropriate expression vector for COS cells, such as pEDΔC or pMT2. The plasmid is transiently transfected into COS cells. The secreted IL-11R-Ig fusion protein is collected in the conditioned medium and purified by protein A chromatography.

The purified IL-11R-Ig fusion protein is used to demonstrate IL-11 binding in a number of applications. IL-11 can be coated onto the surface of an enzyme-linked immunosorbent assay (ELISA) plate, and then additional binding sites blocked with bovine serum albumin or casein using standard ELISA buffers. The IL-11R-Ig fusion protein is then bound to the solid-phase IL-11, and binding is detected with a secondary goat anti-human Ig conjugated to horseradish peroxidase. The activity of specifically bound enzyme can be measured with a colorimetric substrate, such as tetramethyl benzidine and absorbance readings.

IL-11 may also be expressed on the surface of cells, for example by providing a transmembrane domain or glucosyl phosphatidyl inositol (GPI) linkage. Cells expressing the membrane bound IL-11 can be identified using the IL-11R-Ig fusion protein. The soluble IL-11R-Ig fusion is bound to the surface of these cells and detected with goat anti-human Ig conjugated to a fluorochrome, such as fluorescein isothiocyanate and flow cytometry.

Interaction Trap

A yeast genetic selection method, the "interaction trap" [Gyuris et al, Cell 75:791–803, 1993], can be used to determine whether a human IL-11R protein has a biological activity of human IL-11R as defined herein. In this system, the expression of reporter genes from both LexAop-Leu2 and LexAop-LacZ relies on the interaction between the bait protein, for example in this case a species which interacts with huamn IL-11R, and the prey, for example in this case the human IL-11R protein. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

In such methods, if one wishes to determine whether the human IL-11R protein interacts with a particular species (such as, for example, a cystoslic protein which binds to the intracellular domain of the human IL-11R in vivo), that species can be used as the "bait" in the interaction trap with the human IL-11R protein to be tested serving as the "prey", or vice versa.

CAT Induction System

Transcription of acute phase plasma protein genes, such as the rat β-fibrinogen gene, is activated by IL-11 in a variety of cell lines. In one exemplary system, COSM6 cells are cotransfected with plasmids encoding the human IL-11R protein (such as the full length human IL-11R or a soluble form thereof), the human gp130 signal transducer and a reporter gene containing the 350 base pair promoter region of the rat b-fibrinogen gene fused to a reporter gene, CAT (Baumann et al. (1991) J. Biol. Chem. 266, 20424–27). The cells are stimulated with increasing concentrations of recombinant human IL-11 and transcription of the reporter gene is monitored by assaying for the presence of CAT activity.

Phosphorylation of gp130

Activity may also be determined by examining the ability of IL-11 to induce tyrosine phosphorylation of gp130 in cells transfected with a sequence encoding the human IL-11R protein (such as the full length human IL-11R or a soluble form thereof) (Luttcken et al. (1994) Science 263, 89–92).

Phosphorylation of STATs

Activity may also be determined by examining the ability of IL-11 to induce tyrosine phosphorylation of STATs (signal transducers and activators of transcription, a family of DNA binding proteins) in cells transfected with a sequence encoding the human IL-11R protein (such as the full length human IL-11R or a soluble form thereof) (Zhong et al. (1994) Science 264, 95–98).

Phosphorylation of JAK Kinases

Activity may also be determined by examining the ability of IL-11 to induce tyrosine phosphorylation of JAK kinases in cells transfected with a sequence encoding the human IL-11R protein (such as the full length human IL-11R or a soluble form thereof) (Yin et al. (1993) J. Immunol. 151:2555–61).

EXAMPLE 4

Preparation of Soluble Forms

Soluble forms of the human IL-11R proteins were expressed in mammalian cells. The expressed recombinant proteins were capable of transducing a signal in BAF103-9 cells.

Portions of the full length human IL-11R sequence (nucleotides 734–1828 of SEQ ID NO:1 encoding amino acids 1–365 of SEQ ID NO:2; nucleotides 734–1810 of SEQ ID NO:1 encoding amino acids 1–359 of SEQ ID NO:2; nucleotides 734–1768 of SEQ ID NO:1 encoding amino acids 1–345 of SEQ ID NO:2; nucleotides 734–1705 of SEQ ID NO:1 encoding amino acids 1–324 of SEQ ID NO:2) corresponding to soluble forms were cloned into the mammalian expression vector pED an used to transfect COSM6 cells. It is believed that these constructs produced mature proteins beginning with amino acid 23, 24 or 26 of SEQ ID NO:2 and ending with the specified amino acid.

Figure 3:
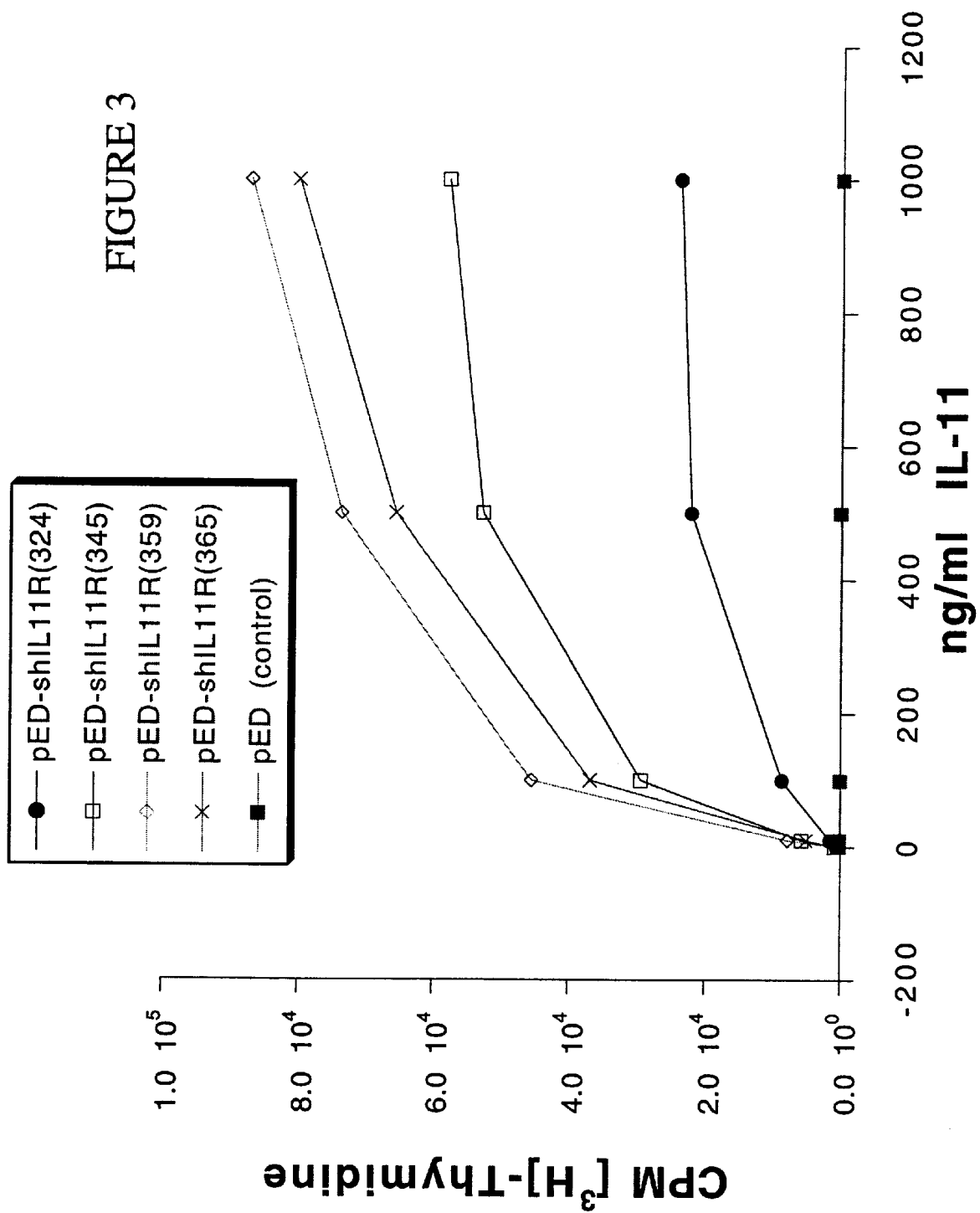
FIG. 3 presents data demonstrating the ability of soluble human IL-11R to mediate cell proliferation in the presence of IL-11.

40 hours after transfection conditioned media was removed, concentrated 5 fold and used in proliferation assays with the murine cell line BAF130-9, a derivative of BAFB03 expressing the human gp130 signal transducer. BAF130-9 cells do not proliferate in response to IL11 or IL6, but do proliferate in response to IL6 and soluble IL6R (Hibi, M. et al. (1990) Cell 63, 1149–57). BAF130-9 cells ($1 \times 10^4$ cell in 0.1 ml) were cultured in RPMI 1640 medium/10% FCS with increasing concentrations of rhIL-11 in the absence or presence of 10 μl of conditioned media from mock transfected cells or cells transfected with the putative soluble hIL11R. After forty hours the cells were pulse-labeled with $^3$H-thymidine (0.5 uCi/well) for four hours and incorporated nucleotide determined. As shown in FIG. 3 BAF130-9 cells do not proliferate in response to IL-11 or soluble IL11R alone but do proliferate in the presence of both IL-11 and any of the soluble forms of the human IL11R.

EXAMPLE 5

IL-11 Binding Assay Involving Soluble Forms

A DNA construct was prepared in which the extracellular domain (corresponding to nucleotides 734–1828 of SEQ ID NO:1 encoding amino acids 1–365 of SEQ ID NO:2 (mature form 23/24/26–365)) was ligated in frame to a cDNA encoding the hinge $C_H2$ and $C_H3$ domains of a human immunoglobulin (Ig) γ1. The resulting cDNA was ligated into pED to generate plasmid pED-Fc-IL11R. A CHO line expressing the fusion protein was generated and the secreted IL-11R-Ig fusion protein was collected from the conditioned media and purified to homogeneity by protein A affinity chromatography.

Figure 4:
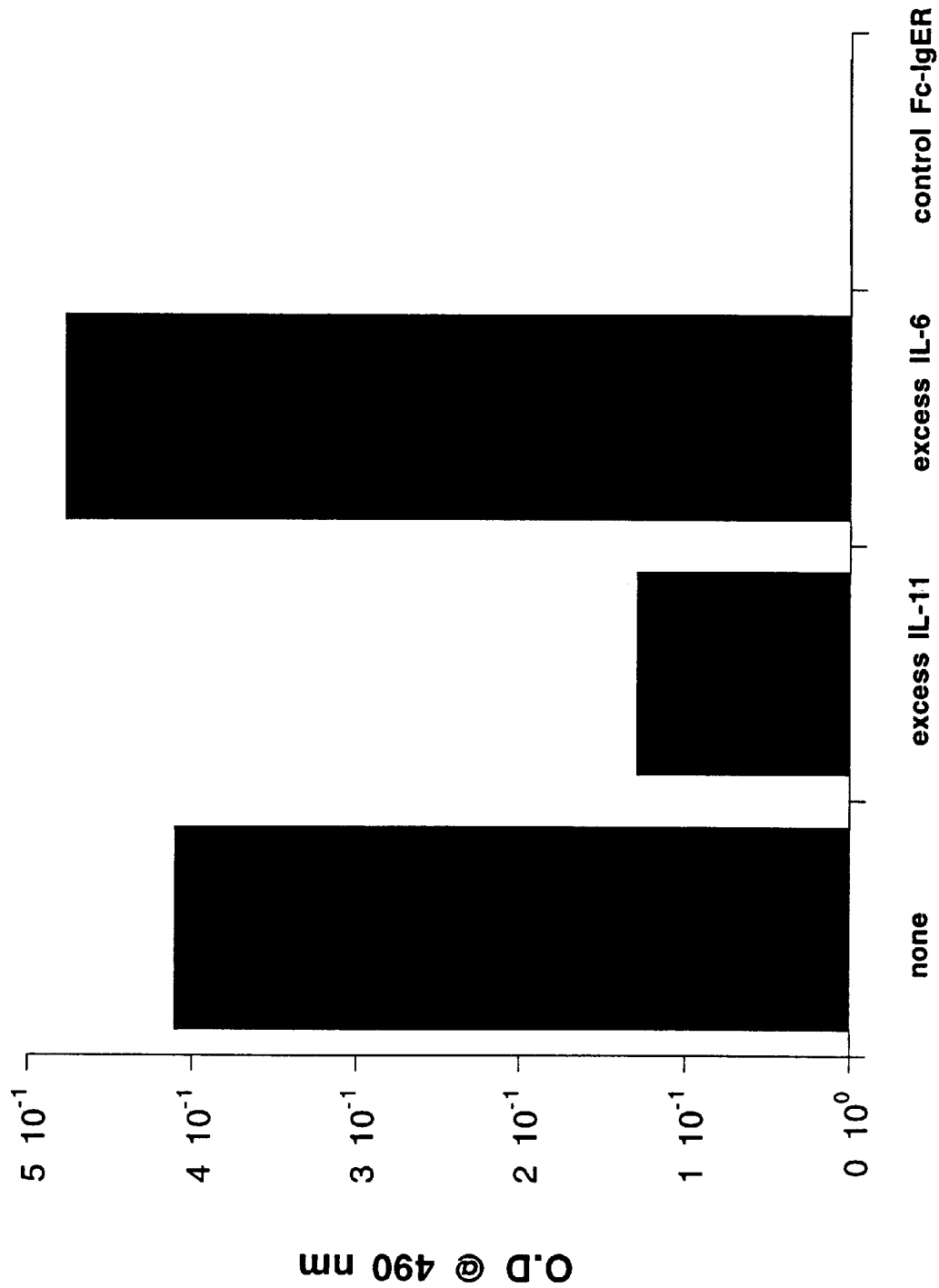
FIG. 4 presents data demonstrating the specific binding of soluble human IL-R protein to IL-11.

The purified IL-11R-Ig fusion protein was used to demonstrate binding to IL-11 in an enzyme-linked immunosorbant assay (ELISA). Briefly, IL-11 was coated onto the surface of an 96-well ELISA plate, and the additional binding sites blocked with casein. The IL-11R-Ig fusion protein was then added to the plate and specific binding was detected using protein A conjugated to horseradish peroxidase. Binding activity was assayed using a calorimetric substrate (tetramethyl benzidine) and monitoring absorbance at 490 nm. As shown in FIG. 4, the IL-11R-Ig fusion protein binds to the IL-11 coated plates, whereas an IgERa-Ig fusion protein does not. Furthermore, the binding specific since it can be competed if the IL-11R-Ig fusion protein is first preincubated with an excess of IL-11 but not with IL-6.

All patent and literature references cited herein are incorporated by reference as if fully set forth.

What is claimed is:

1. An isolated human interleukin-11 receptor (IL-11R) protein free of other human proteins, comprising an amino acid sequence selected from the group consisting of:
   (a) the amino acid sequence of SEQ ID NO:2;
   (b) the amino acid sequence of SEQ ID NO:2 from amino acids 24 to 422;
   (c) the amino acid sequence of SEQ ID NO:2 from amino acids 24 to 365;
   (d) the amino acid sequence of SEQ ID NO:2 from amino acids 391 to 422;
   (e) the amino acid sequence of SEQ ID NO:2 from amino acids 112 to 422;
   (f) the amino acid sequence of SEQ ID NO:2 from amino acids 112 to 365;
   (g) the amino acid sequence of SEQ ID NO:2 from amino acids 24 to 359;
   (h) the amino acid sequence of SEQ ID NO:2 from amino acids 24 to 345; and
   (I) the amino acid sequence of SEQ ID NO:2 from amino acids 24 to 324.

2. The protein of claim 1 comprising the amino acid sequence of SEQ ID NO:2.

3. The protein of claim 1 comprising the sequence from amino acid 24 to 365 of SEQ ID NO:2.

4. The protein of claim 1 comprising an amino acid sequence beginning at amino acid 26 of SEQ ID NO:2.

5. The protein of claim 1 comprising an amino acid sequence beginning at amino acid 23 of SEQ ID NO:2.

6. The protein of claim 1 comprising an amino acid sequence beginning at amino acid 1 of SEQ ID NO:2.

7. The protein of claim 1 comprising the amino acid sequence of SEQ ID NO:2 from amino acids 24 to 422.

8. The protein of claim 1 comprising the amino acid sequence of SEQ ID NO:2 from amino acids 391 to 422.

9. The protein of claim 1 comprising the amino acid sequence of SEQ ID NO:2 from amino acids 112 to 422.

10. The protein of claim 1 comprising the amino acid sequence of SEQ ID NO:2 from amino acids 112 to 365.

11. The protein of claim 1 comprising the amino acid sequence of SEQ ID NO:2 from amino acids 24 to 359.

12. The protein of claim 1 comprising the amino acid sequence of SEQ ID NO:2 from amino acids 24 to 345.

13. The protein of claim 1 comprising the amino acid sequence of SEQ ID NO:2 from amino acids 24 to 324.

* * * * *